(12) United States Patent
Jin

(10) Patent No.: US 8,599,375 B2
(45) Date of Patent: Dec. 3, 2013

(54) ATOMIC ABSORPTION INSTRUMENT

(75) Inventor: Feng Jin, Milford, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 400 days.

(21) Appl. No.: 12/962,342

(22) Filed: Dec. 7, 2010

(65) Prior Publication Data

US 2012/0140218 A1    Jun. 7, 2012

(51) Int. Cl.
*G01J 3/30* (2006.01)
*F23D 14/62* (2006.01)

(52) U.S. Cl.
USPC .......................................... 356/315; 431/354

(58) Field of Classification Search
USPC .......... 356/315, 317, 36; 431/354, 126, 4, 14, 431/79, 89
See application file for complete search history.

(56) References Cited

U.S. PATENT DOCUMENTS

| | | | | |
|---|---|---|---|---|
| 3,208,333 A | * | 9/1965 | Gilbert, Jr. .................... | 356/315 |
| 3,438,711 A | * | 4/1969 | Hell .............................. | 356/36 |
| 3,525,476 A | | 8/1970 | Boling et al. ................. | 239/338 |
| 3,810,583 A | * | 5/1974 | George ......................... | 239/597 |
| 3,879,126 A | * | 4/1975 | Delew .......................... | 356/315 |
| 4,125,225 A | | 11/1978 | Venghiattis .................... | 239/338 |
| 4,367,042 A | | 1/1983 | Smith, Jr. et al. ............. | 356/315 |
| 4,568,267 A | | 2/1986 | Kendall-Tobias ............... | 431/90 |
| 4,606,718 A | | 8/1986 | Kendall-Tobias ............... | 431/6 |
| 4,660,976 A | * | 4/1987 | Falk .............................. | 356/312 |
| 4,776,694 A | | 10/1988 | Rogasch et al. ............... | 356/315 |
| 4,886,359 A | | 12/1989 | Berndt ........................... | 356/312 |
| 4,948,185 A | * | 8/1990 | Miller ........................... | 292/256.5 |
| 6,222,626 B1 | | 4/2001 | Radziuk et al. ................ | 356/307 |
| 6,829,048 B2 | | 12/2004 | Erath ............................. | 356/315 |
| 7,866,317 B2 | * | 1/2011 | Muellinger et al. ........... | 128/204.18 |
| 2002/0006591 A1 | * | 1/2002 | Hugens, Jr. .................... | 431/8 |
| 2005/0230498 A1 | | 10/2005 | Ruediger et al. .............. | 239/338 |

FOREIGN PATENT DOCUMENTS

| | | |
|---|---|---|
| DE | 34 44 640 A1 | 6/1986 |
| DE | 296 17 621 U1 | 10/1997 |
| DE | 101 22 873 A1 | 11/2002 |
| WO | 2007/035132 A2 | 3/2007 |

OTHER PUBLICATIONS

Invitation to Pay Additional Fees/Communication Relating to the Results of the Partial International Search, mailed Nov. 7, 2011, for counterpart PCT/US2010/059285, 7 pages.

\* cited by examiner

*Primary Examiner* — Gregory J Toatley
*Assistant Examiner* — Shawn Decenzo
(74) *Attorney, Agent, or Firm* — Seed IP Law Group PLLC

(57) ABSTRACT

An atomic absorption instrument has a burner and a mixing apparatus for delivering a combustible mixture to the burner. The mixing apparatus includes a mixing chamber assembly having a plurality of internal delivery passageways. An end cap assembly holds a nebulizer closes a mixing chamber. The end cap assembly has a plurality of internal feed passageways through which fluid from the internal delivery passageways flows into the mixing chamber. Latch mechanisms couple the end cap assembly to the mixing chamber assembly. The latch mechanisms can be operated to remove the end cap assembly.

19 Claims, 16 Drawing Sheets

ATOMIC ABSORPTION INSTRUMENT

BACKGROUND

1. Technical Field

The present disclosure is related to absorption instruments and, more particularly, to atomic absorption instruments with burner systems.

2. Description of the Related Art

Spectroscopy instruments are often used to analyze a sample. Atomic spectroscopy instruments can determine the presence and concentration of elements (e.g., metals) in liquid samples based on absorption, scattering, emission, or fluorescence by atoms, molecules, and/or elementary ions. Absorption involves the transfer of electromagnetic energy from a source to an atom or molecule. Scattering involves the redirection of light due to the light's interaction with molecules. Emission involves electromagnetic energy moving from one energy level to another energy level resulting in the emission of a photon. For example, an atom in a ground state can absorb light such that the atom reaches an excited state. The amount of absorbed electromagnetic energy increases as the number of atoms of a selected element increases. Based on the amount of absorbed electromagnetic energy, the sample concentration can be determined.

Flame atomic absorption instruments are a type of spectroscopy instrument that can determine the composition of a liquid sample. A nebulizer can produce a fine mist of sample droplets that are mixed with a fuel and an oxidant. The combustible mixture is delivered to a burner. The burner outputs the combustible mixture to maintain a flame in which the sample is vaporized and element(s) of interest are atomized. Light is delivered through the flame, and based on the amount of energy absorbed by the element(s) of interest in the flame, the presence and/or concentration of the element(s) of interest in the sample can be determined.

BRIEF SUMMARY

Some embodiments disclosed herein are directed to an atomic absorption instrument including a burner for burning a combustible mixture and a mixing apparatus for delivering the combustible mixture to the burner. Advantageously, the mixture can be produced without utilizing complicated external hosing arrangements. Internal fluid lines can deliver fluids to the mixing apparatus. The fluids are combined in an internal chamber of the mixing apparatus and delivered to the burner.

A mixing apparatus, in some embodiments, includes a mixing chamber assembly with internal delivery passageways and an internal mixing chamber. A rigid elongate main body defines a portion of the chamber and carries a burner. An end cap assembly is configured to hold a nebulizer and to close the chamber. The end cap assembly includes a manifold that fluidically couples the delivery passageways to the chamber.

In some embodiments, a spectroscopy instrument includes a burner and a mixing apparatus for delivering a combustible mixture to the burner. The mixing apparatus includes a mixing chamber assembly that delivers fluids to an end cap assembly. The end cap assembly holds a nebulizer and covers a mixing chamber and also delivers fluids from the mixing chamber assembly to the chamber. In certain embodiments, the end cap assembly includes a plurality of internal feed passageways that deliver fluid that flows out of internal delivery passageways of the chamber assembly to the mixing chamber. The fluids mix and flow through the mixing chamber to the burner.

In certain embodiments, a spectroscopy instrument includes a modular mixing apparatus receivable by a base unit to establish fluid communication between the base unit and an internal mixing chamber. An end cap assembly can be removed to open the internal mixing chamber. One or more latching mechanisms can couple the end cap assembly to a multi-lumen main body carrying a burner.

In some embodiments, a mixing apparatus for a spectroscopy instrument includes one or more internal passageways that fluidically couple to internal fluid lines of a base unit. Latch mechanisms can be operated to release an end cap assembly to, for example, perform maintenance, inspect internal components, replace internal components, or the like.

In yet other embodiments, a two-way flow mixing chamber assembly is configured to deliver a combustible mixture to a burner of an atomic absorption instrument. The combustible mixture flows in a first direction through an internal mixing chamber towards the burner. Fuel, oxidant, compressed air, and/or other types of fluids can flow through the mixing chamber assembly in a second direction that is opposite to the first direction. In some embodiments, the fluids can flow through an end cap assembly and into the chamber to produce the mixture. In certain embodiments, the combustible mixture flowing in the first direction can flow upwardly through a slot in the burner.

In some embodiments, a spectroscope instrument has a mixing apparatus that receives fluids for producing a combustible mixture from a base unit to reduce the number of external hoses and conduits in front of the instrument. Conventional atomic absorption instruments often include at least three external hoses that deliver substances for producing a combustible mixture. Conventional hoses are often difficult to handle, prone to leakage, unsightly, and may cause other problems. The internal fluid delivery system with internal passageway provides a user friendly instrument.

In some other embodiments, an atomic absorption instrument includes a burner and a mixing apparatus for delivering a combustible mixture to the burner. The mixing apparatus includes a mixing chamber assembly that includes a main body and a plurality of internal delivery passageways extending through the main body towards an end of the mixing chamber assembly. In certain embodiments, the internal delivery passageways are located between an exterior surface of the main body and an interior surface of the main body. The interior surface defines at least a portion of a mixing chamber through which the combustible mixture flows towards the burner. An end cap assembly is configured to hold a nebulizer. The end cap assembly includes a plurality of internal feed passageways through which fluid from the internal delivery passageways flows into the mixing chamber when the end cap assembly is coupled to the end of the mixing chamber assembly.

A mixing apparatus for an atomic absorption instrument, in some embodiments, may be summarized as including one or more longitudinally-extending internal lumens in a main body. The internal lumens are configured to deliver at least one fluid towards a portion of the mixing apparatus configured to carry a nebulizer. An internal mixing chamber in the main body can receive a spray from the nebulizer. The mixing chamber extends from the internal lumens to a burner. The burner can be coupled to the mixing apparatus.

In certain embodiments, an end cap assembly for a mixing apparatus of an atomic absorption instrument includes a first face for mating with a mixing chamber assembly, a second face opposing the first face, and a nebulizer receiving channel extending through a main body. The first face can contact or be spaced apart from the mixing chamber assembly.

The nebulizer receiving channel is dimensioned such that a port of a nebulizer is positioned within the nebulizer receiving channel and an outlet of the nebulizer is positioned to deliver a spray in a mixing chamber when the end cap assembly carries the nebulizer and is coupled to the mixing chamber assembly. A manifold includes a plurality of fluid passageways extending from the first face. One of the fluid passageways delivers a first fluid from the mixing chamber assembly to the nebulizer and another one of the passageways delivers a second fluid from the mixing chamber assembly to the mixing chamber. The first and second fluids can be delivered concurrently or sequentially.

In yet other embodiments, an atomic absorption instrument may be summarized as including a mixing chamber assembly including a main body, an internal chamber for delivering a mixture to a burner, and an end cap assembly coupleable to the main body. The end cap assembly is configured to hold a nebulizer that delivers a sample into the internal chamber. One or more latch mechanisms are movable between an unlatch configuration and a latched configuration to couple the end cap assembly to the main body.

A method of assembling an atomic absorption instrument may be summarized as including moving an end cap assembly towards an end of a mixing chamber assembly. The end cap assembly is configured to hold a nebulizer that delivers an atomized sample to a mixing chamber. At least one latch mechanism is moved from an unlatched configuration to a latched configuration to pull the end cap assembly towards the mixing chamber assembly so as to sealingly couple the end cap assembly to the mixing chamber assembly.

BRIEF DESCRIPTION OF THE SEVERAL VIEWS OF THE DRAWINGS

Non-limiting and non-exhaustive embodiments are described with reference to the following drawings. The same reference numerals refer to like parts or acts throughout the various views, unless otherwise specified.

DETAILED DESCRIPTION

Figure 1:
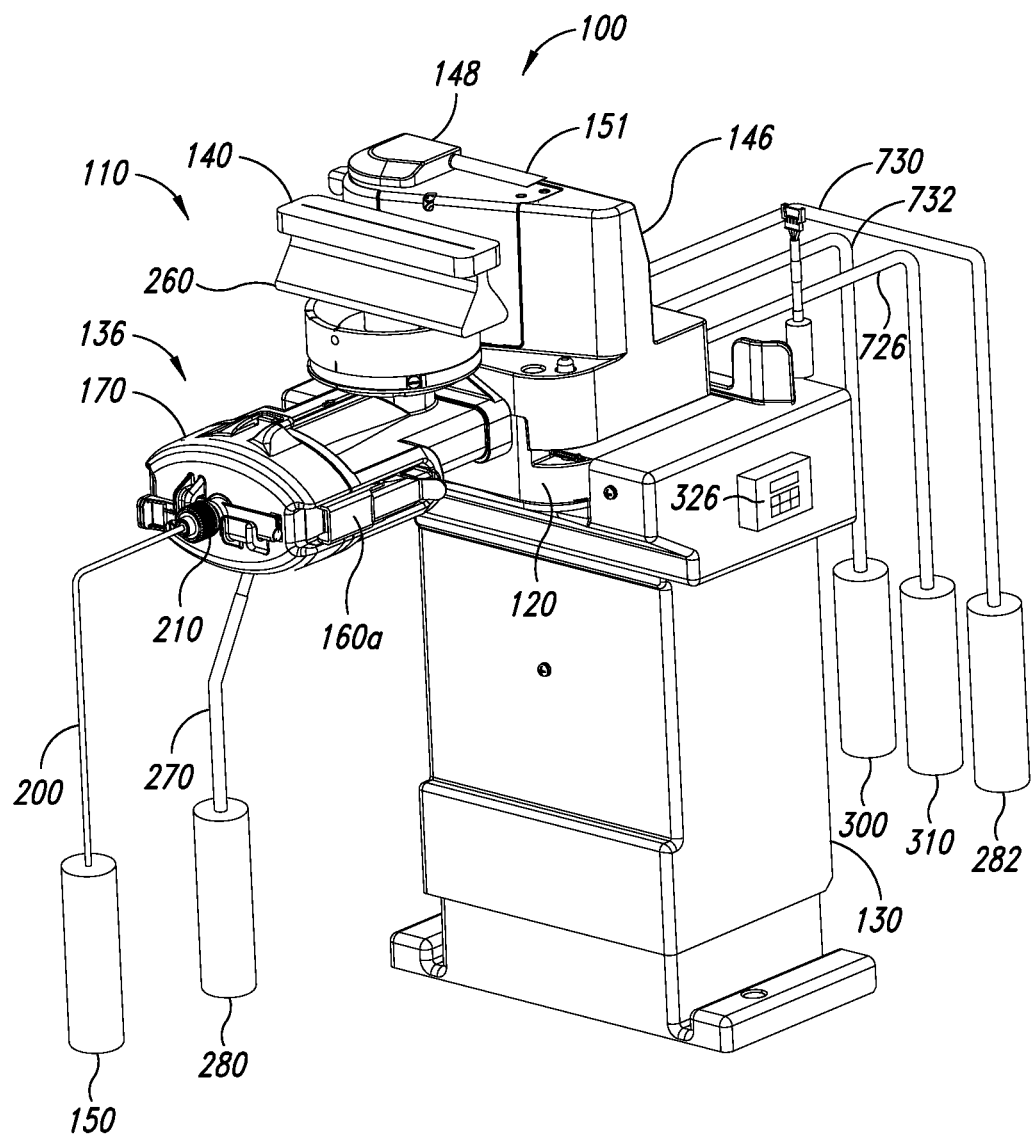
FIG. 1 is an isometric view of an absorption instrument, in accordance with one embodiment.

FIG. 1 shows an absorption instrument in the form of a flame atomic absorption ("AA") instrument 100 capable of analyzing a sample. The AA instrument 100 includes a burner system 110, a docking station 120, and a base unit 130. The burner system 110 includes a mixing apparatus 136, a burner 140, and an ignition system 146. A combustible mixture comprising a sample can be prepared in the mixing apparatus 136. The combustible mixture can be combusted to reduce atoms of element(s) of interest to free, unexcited atoms in a ground state suitable for optical analysis. The sample can be analyzed to determine the presence of element(s), concentration of element(s), or other types of detectable characteristics. The instrument 100 has internal passageways through which fluids for producing the mixture flow.

The base unit 130 can deliver substances (e.g., fuel, oxidant, pressurized gas, or other flowable substances) to the docking station 120, which in turn delivers the substances to the mixing apparatus 136. The substances can flow through and be combined inside of the mixing apparatus 136. This alleviates or eliminates problems associated with external fuel hoses, oxidant hoses, and pressurized gas hoses often used with conventional absorption instruments. Conventional absorption instruments often include at least three external hoses that deliver substances for producing a combustible mixture. Conventional hoses are often difficult to handle, prone to leakage, and may cause other problems. The base unit 130 alleviates or eliminates these types of problems.

The ignition system 146 is carried on the base unit 130 and includes a rotatable igniter 148. An end 151 of the igniter 148 can be rotated from a standby position (illustrated in FIG. 1) to an ignition position. When the igniter 148 is in the ignition position, the end 151 is positioned generally over the burner

140 to ignite the combustible mixture. After igniting the mixture, the igniter 148 can be moved to the standby position.

A user can manually operate latch mechanisms 160a, 160b (FIG. 3) to conveniently remove and replace an end cap assembly 170 or other components (e.g., a nebulizer). The end cap assembly 170 can be removed in order to inspect components, replace components, perform maintenance (e.g., clean or realign components), or the like. The end cap assembly 170 conveniently self-aligns to form seals to prevent unwanted leakage when secured by the latch mechanisms 160a, 160b.

Figure 2:
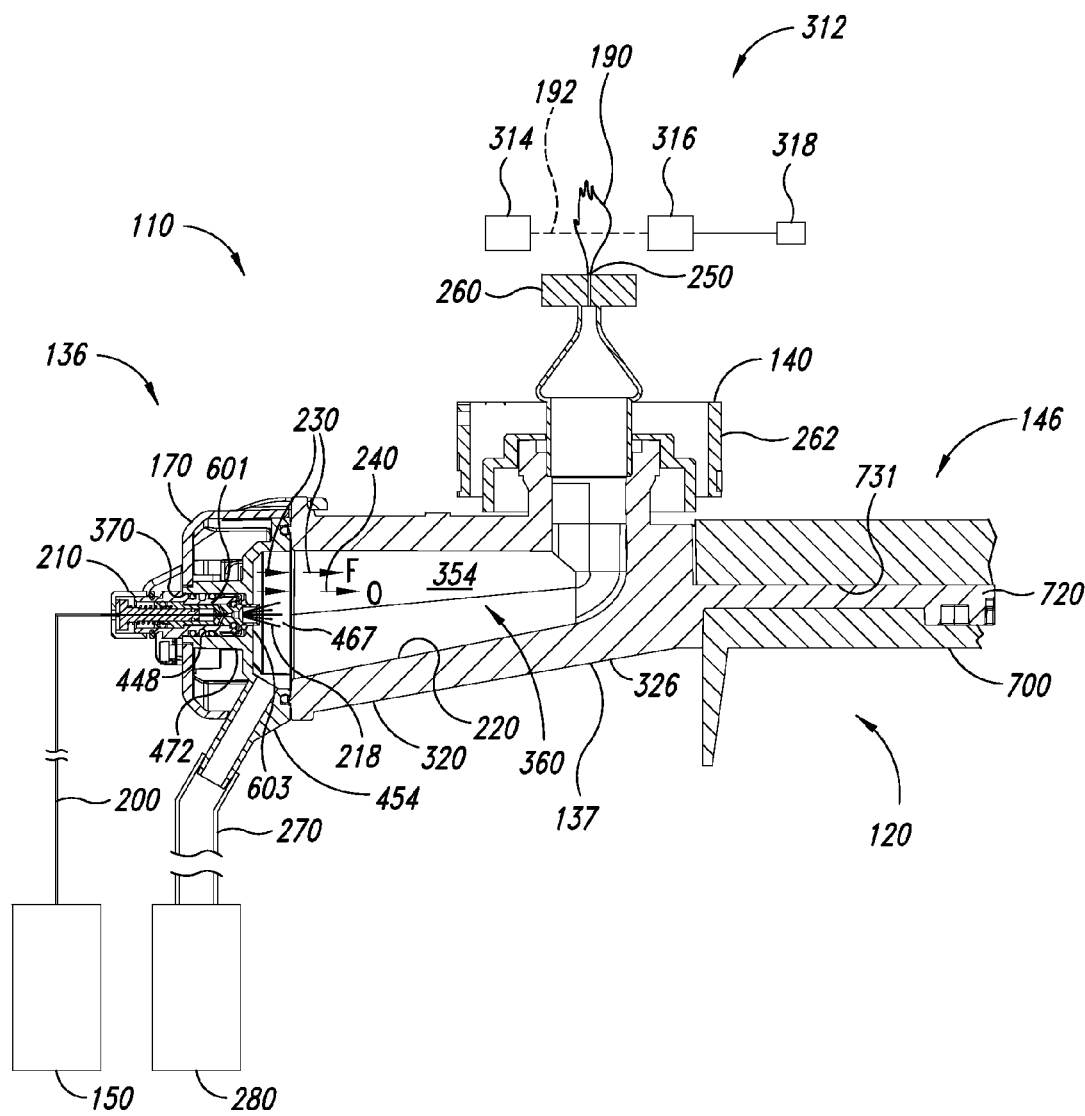
FIG. 2 is a partial cross-sectional view of components of an absorption instrument with a burner system for producing a flame and an optical detection system for analyzing the flame, in accordance with one embodiment.

Referring to FIGS. 1 and 2, a sample source 150 delivers a liquid sample through a conduit 200 to a nebulizer 210. The nebulizer 210 produces a sample spray 218 that is mixed with one or more substances (e.g., one or more fuels, oxidants, or other suitable substances). FIG. 2 shows a fuel F and an oxidant O flowing through a mixing chamber 220, as indicated by arrows 230, 240. The sample spray 218, fuel F, and oxidant O are mixed together to form a combustible mixture, and the combustible mixture flows through a slot 250 in a burner head 260 and is combusted to produce a flame 190.

The burner 140 can generally include a sensor 262 that can be used to determine the position of the burner head 260. The sensor 262 can be a magnetic ring sensor or other type of position sensor. A gas box system can be used to increase or decrease the flow rate of the combustible mixture. The flow rate, percentages by weight or volume of constituents in the combustible mixture, and other characteristics of the combustible mixture can be adjusted by adjusting the flow rates of the fuel F, oxidant O, working pressures, etc. Residue, excess liquid, or other waste material can be drained through a waste conduit 270 and delivered to a waste receptacle 280.

Referring again to FIG. 1, the instrument 100 can include, without limitation, a fuel source 282, an oxidant source 300, and a pressurized fluid source 310. The sources 282, 300, and 310 can include, without limitation, one or more containers (e.g., canisters, bottles, tanks, or the like), pressurization devices (e.g., pumps, compressors, etc.), filers, thermal devices, valves, or the like. For example, the pressurized fluid source 310 can include one or more air compressors. The fuel source 282 can include, without limitation, one or more containers holding natural gas, methane, hydrogen, acetylene, mixtures thereof, or other types of fuels. The oxidant source 300 can include, without limitation, one or more containers holding air, oxygen, nitrous oxide, mixtures thereof, or other types of oxidants.

If an instrument has a plurality of mixing apparatuses for concurrently analyzing different samples, a plurality of pressurized gas sources, a plurality of fuel sources, and a plurality of oxidant sources can independently deliver substances to the mixing apparatuses. The base unit 130 can also include, without limitation, one or more motors, solenoids, robotic arms, linear slides, XYZ mechanisms, or other components suitable for rotating, translating, or otherwise moving parts of the instrument 100. In some embodiments, an XYZ mechanism can move the docking station 120 and the igniter 148.

A controller 326 of FIG. 1 can generally include, without limitation, one or more computers, central processing units, processing devices, microprocessors, digital signal processors, central processing units, processing devices, microprocessors, digital signal processors (DSP), application-specific integrated circuits (ASIC), readers, and the like. To store information, the controller 326 includes, without limitation, one or more storage elements, such as volatile memory, non-volatile memory, read-only memory (ROM), random access memory (RAM), or the like. The stored information can include, without limitation, optimization programs, operating pressure programs, calibration programs, or other executable programs. The controller 326 can execute optimization programs to produce optimal flames for optical analysis. Working pressures may be optimized by determining, for example, optimum flow rates of fuels, oxidants, pressurized fluids, etc. The controller 326 can be communicatively coupled to different components of the instrument 100, including, but not limited to, sensors, the sources 282, 310, 300, the ignition system 146, and may include a display that outputs information to a user. A keyboard, a control panel, a touch screen, or other device(s) can be used to input information. In some embodiments, sensors send signals to the controller 326 indicating whether components (e.g., the nebulizer 210) are properly installed and/or functioning. A user can be notified if components need to be cleaned, replaced, realigned, or reinstalled.

Referring to FIG. 2, an optical detection system 312 generally includes a light source 314, a light separator 316, and a detector 318. Light from the light source 314 passes through the flame 190 and reaches the light separator 316. During combustion, atoms of the element of interest in the sample can be reduced to free, unexcited atoms in the ground state. The atoms can absorb light at one or more characteristic wavelengths, which can be element specific. The amount of reduction of light intensity due to absorption can be directly related to the amount of the element of interest (e.g., analyte) in the sample. In this manner, the optical detection system 312 can evaluate the concentration or presence of at least one element of interest.

The detector 318 can be part of the controller 326. In other embodiments, the detector 318 is a separate component that communicates (e.g., wirelessly) with the controller 326. The controller 326 can process the information from the detector 318 to command the instrument 100, generate reports, output data, or the like.

The light source 314 may include, without limitation, one or more lamps (e.g., cathode lamps), lasers, light emitting panels (e.g., panels of LEDs), or other suitable sources. The light separator 316 can be a monochromator that isolates the analytical line photons that have passed through the flame 190. Other types of light separators can be used to remove any number of wavelengths to provide a generally narrow spectral line.

A wide range of different types of optical components can be positioned along a light path 192. The optical components can include, but are not limited to, lenses, mirrors, filters, or the like. The types and positions of the optical components can be selected based on the type of analysis to be performed.

Figure 3:
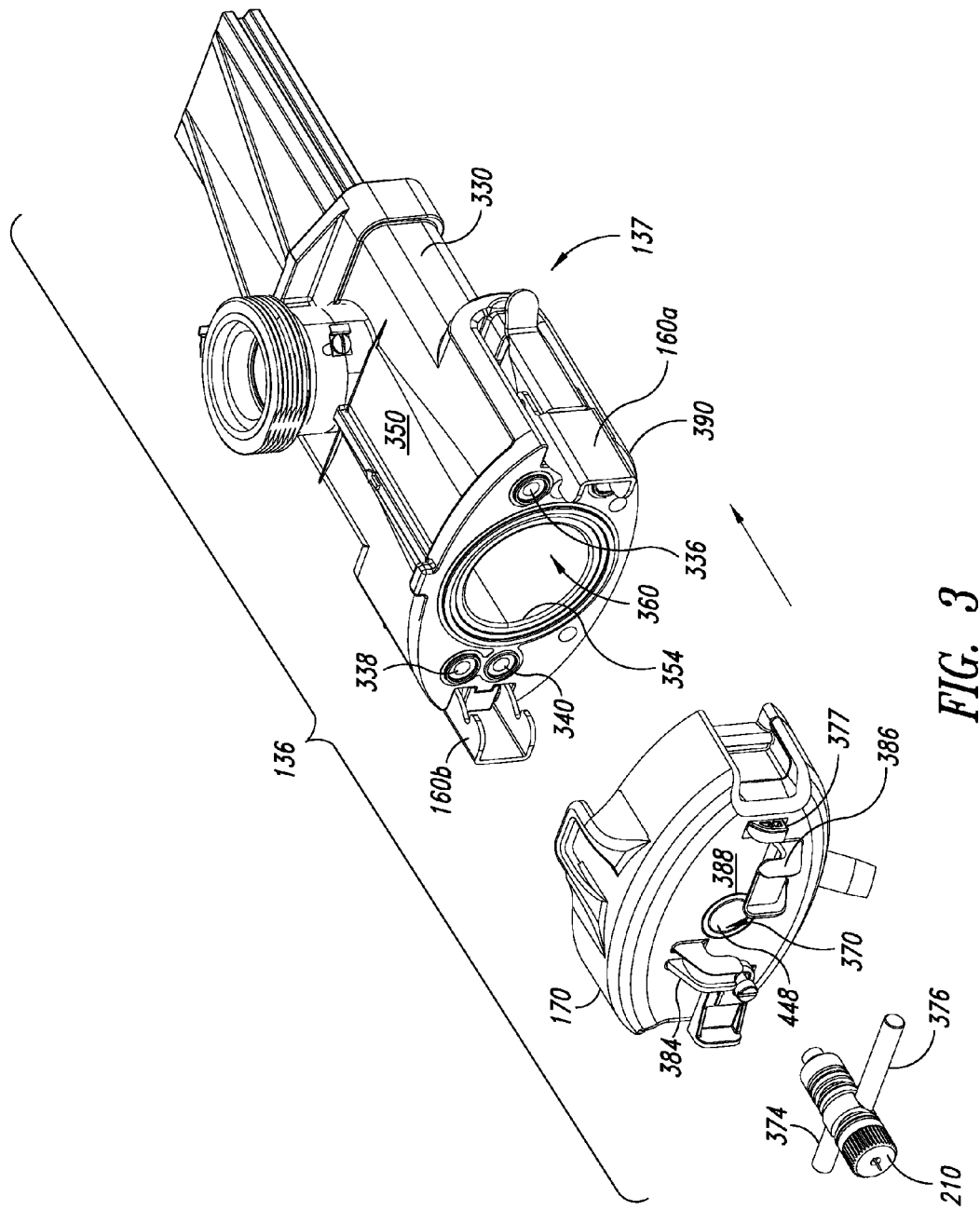
FIG. 3 is an exploded isometric view of a mixing apparatus, in accordance with one embodiment.

FIGS. 2 and 3 show a mixing chamber assembly 137 that delivers a pressurized fluid to the end cap assembly 170, which feeds the pressurized fluid to the nebulizer 210. The pressurized fluid flows through the nebulizer 210 to generate the spray 218. A multi-directional flow main body 330 has internal delivery passageways 336, 338, 340 and a lumen 360. The delivery passageways 336, 338, 340 are positioned between an exterior surface 350 and an interior surface 354. The interior surface 354 forms a section of the mixing chamber 220 downstream of the end cap assembly 170.

Molding processes, machining processes, and/or other types of manufacturing processes can be used to form the main body 330. The portion of the main body 330 that defines the delivery passageways 336, 338, 340 can have a unitary construction and can be formed of one or more metals, plastics, polymers, composites, combinations thereof, or the like. Alternatively, the delivery passageways 336, 338, 340 can be formed by conduits (e.g., tubes, hoses, etc.) that are molded or inserted into the main body 330.

To install the nebulizer 210 of FIG. 3, the nebulizer 210 can be inserted through an opening 370. Arms 374, 376 can be moved between tabs 384, 386 and a front face 388. A sensor 377 can detect the arm 376 to determine whether the nebulizer 210 is properly installed. Once the nebulizer 210 is locked in place, the latch mechanisms 160a, 160b can be used to pull the end cap assembly 170 against an end 390 to close and seal the mixing chamber 220.

Figure 4:
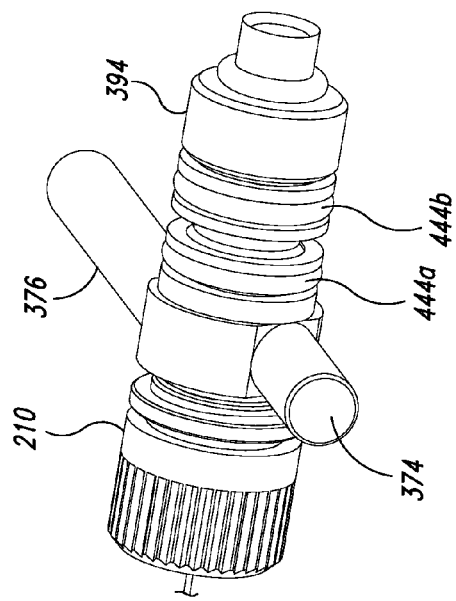
FIG. 4 is an isometric view of a nebulizer, in accordance with one embodiment.
Figure 6:
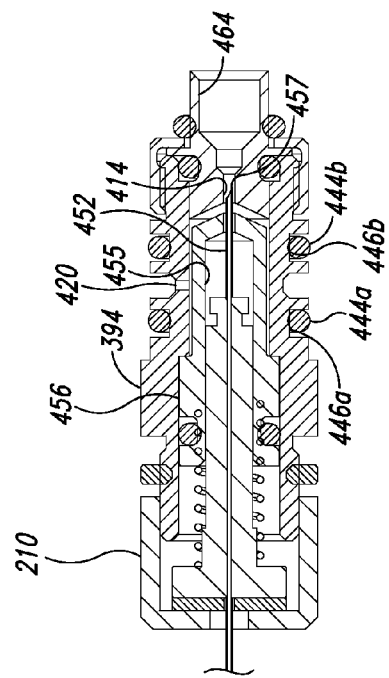
FIG. 6 is a cross-sectional view of the nebulizer taken along a line 6-6 of FIG. 5.
Figure 5:
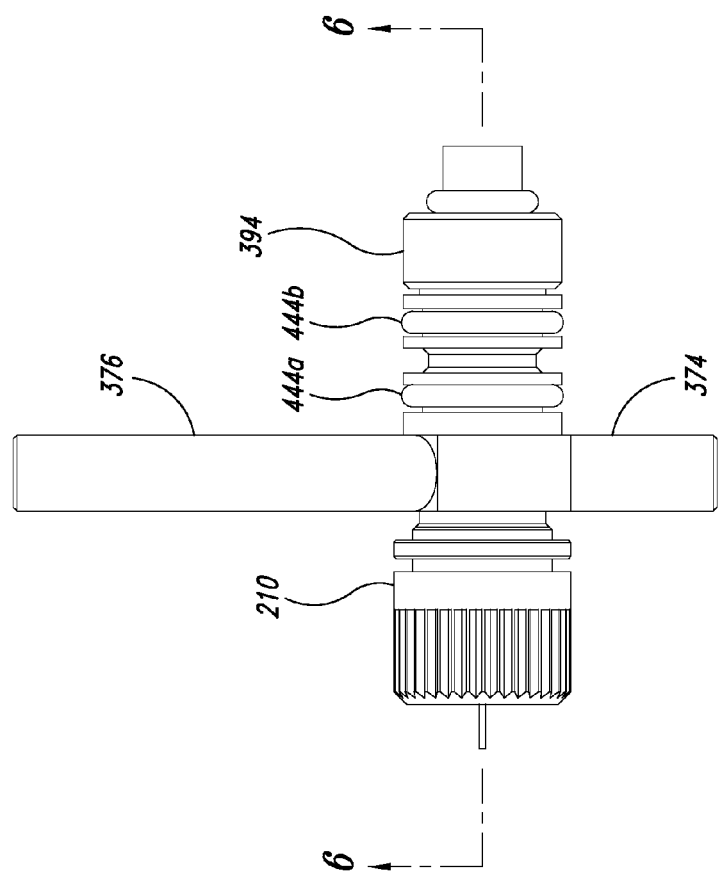
FIG. 5 is a plan view of the nebulizer of FIG. 4.
Figure 7:
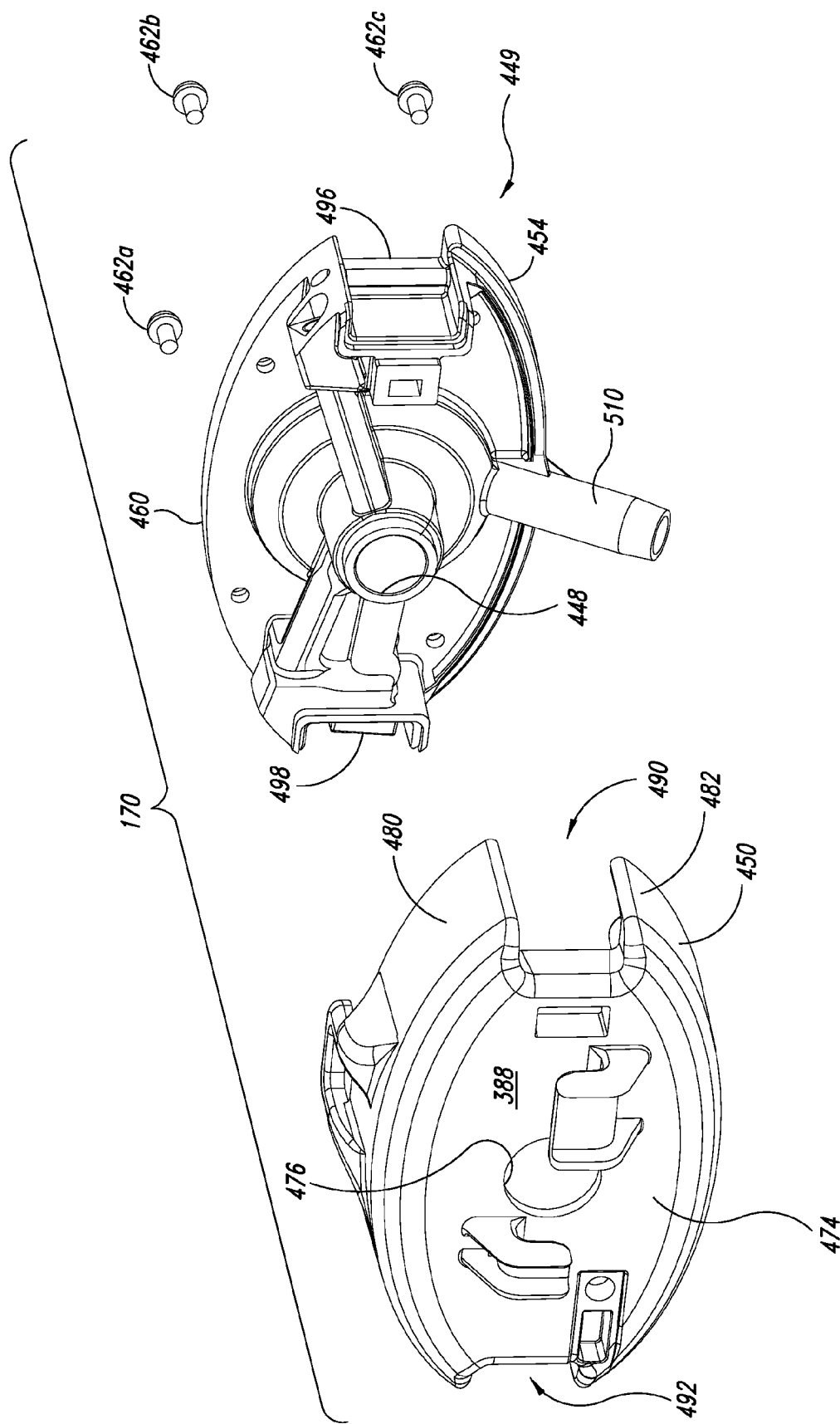
FIG. 7 is an exploded front, top, and left side isometric view of an end cap assembly, in accordance with one embodiment.
Figure 8:
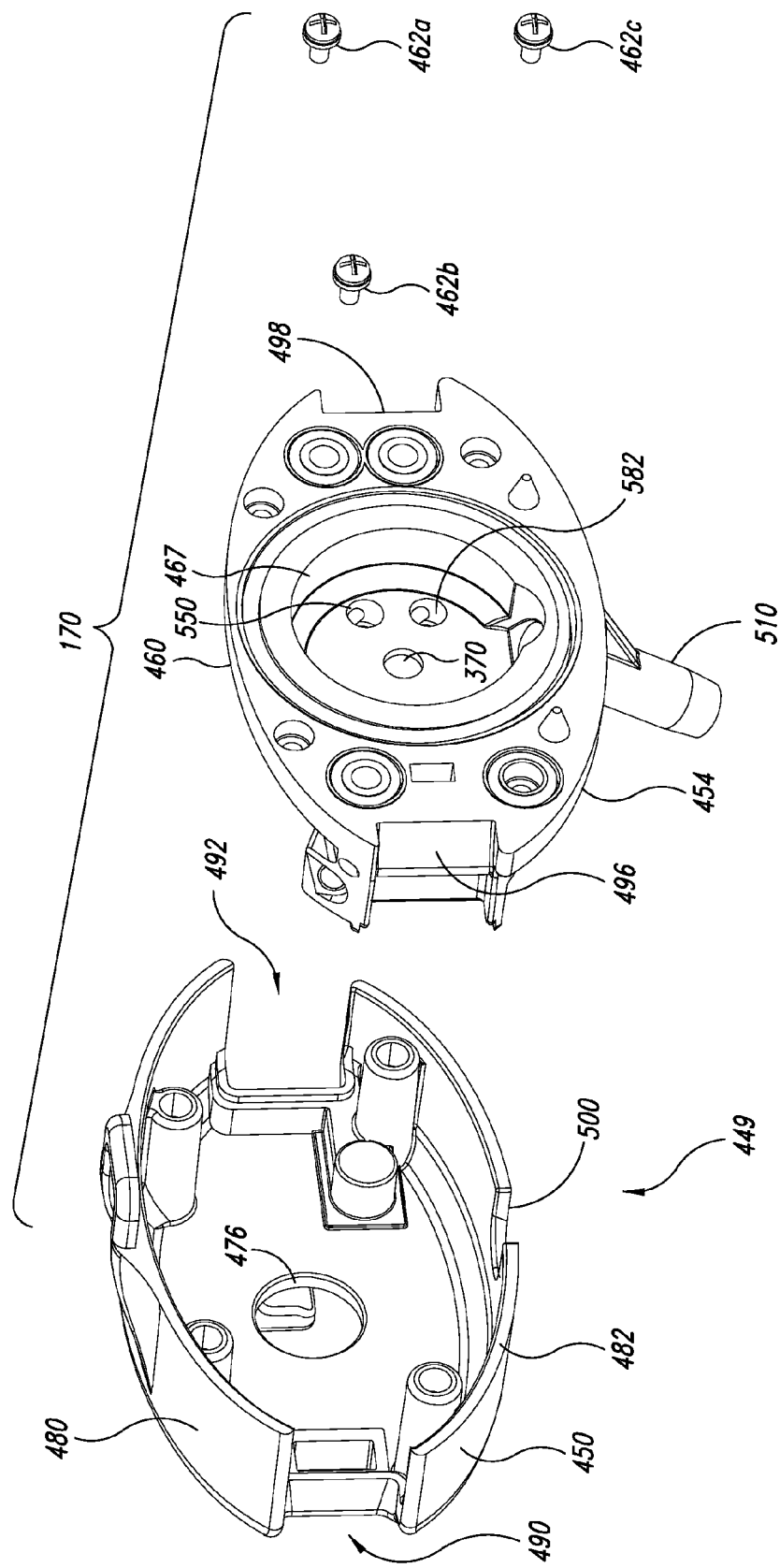
FIG. 8 is an exploded rear, top, and left side isometric view of the end cap assembly of FIG. 7.
Figure 9:
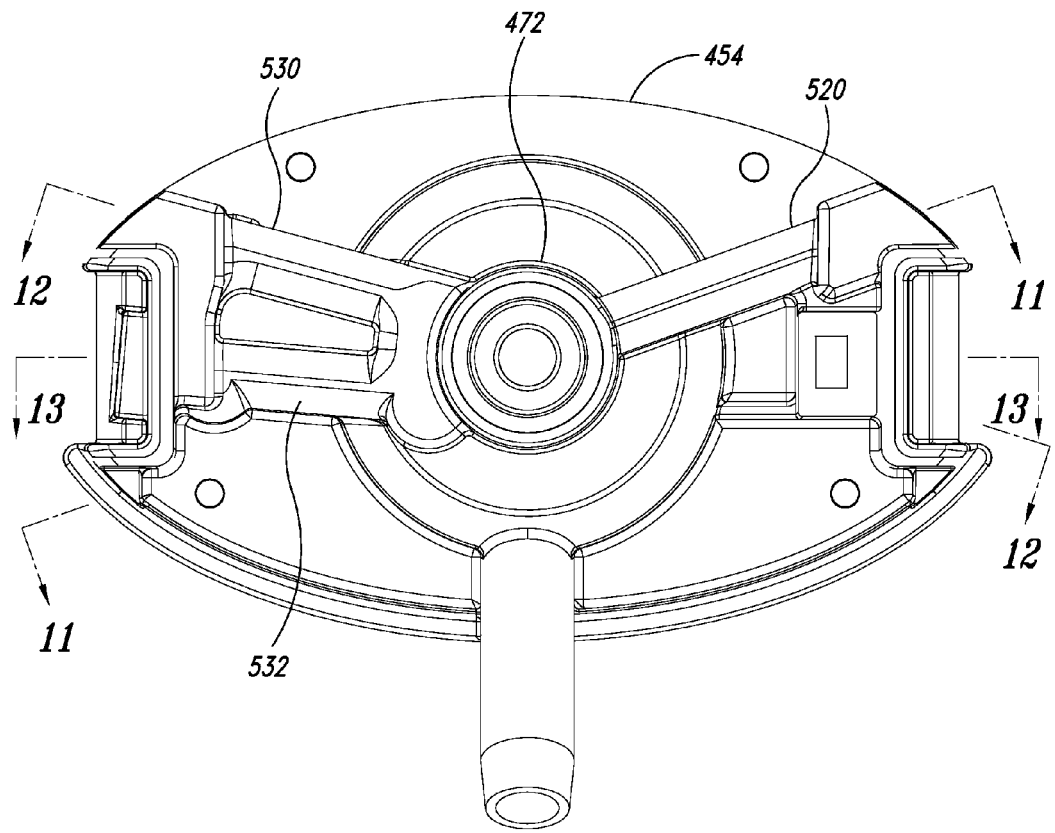
FIG. 9 is a front elevational view of a manifold of an end cap assembly.
Figure 10:
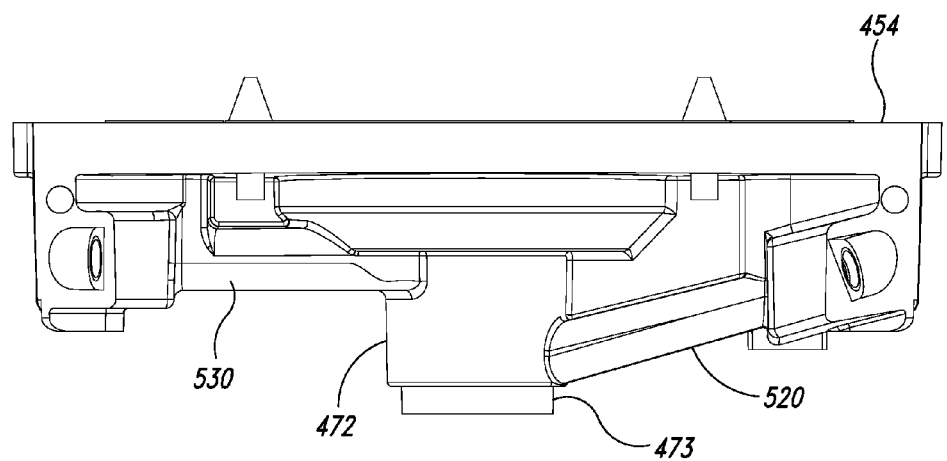
FIG. 10 is a plan view of the manifold of FIG. 9.

FIGS. 4-6 show the nebulizer 210 including an outer housing 394 with the outwardly extending arms 374, 376 and a port 420. The port 420 is position between sealing members 444a, 444b (collectively "444") disposed within annular grooves 446a, 446b, respectively. The sealing members 444 can form seals with a surface 448 (FIGS. 2 and 3) defining the opening 370. The sealing members 444 can be O-rings, compressible members, or other types of one-piece members or multi-piece members capable of deforming or bearing against the surface 448 to form seals, such as airtight seals, hermetic seals, watertight seals, or the like.

Figure 11:
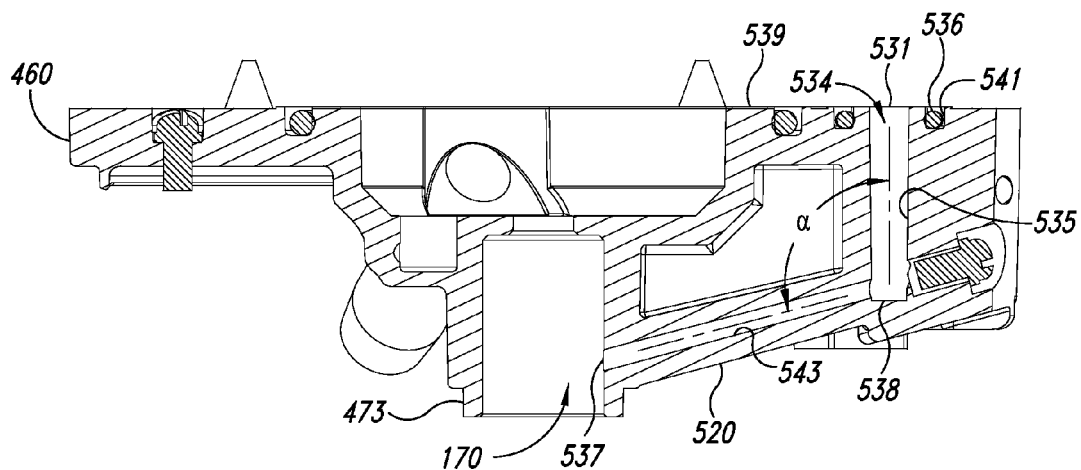
FIG. 11 is a cross-sectional view of the manifold of FIG. 9 taken along a line 11-11.
Figure 12:
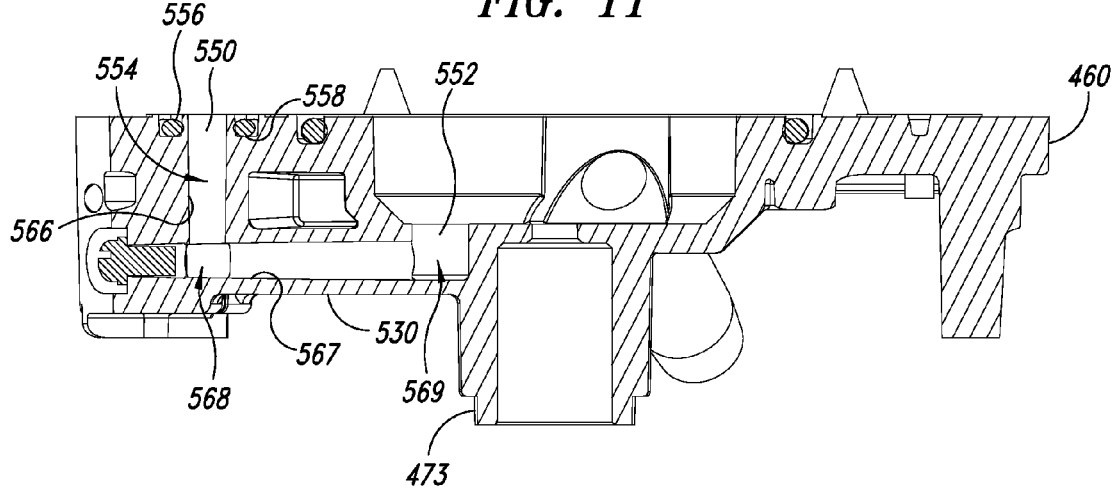
FIG. 12 is a cross-sectional view of the manifold of FIG. 9 taken along a line 12-12.
Figure 13:
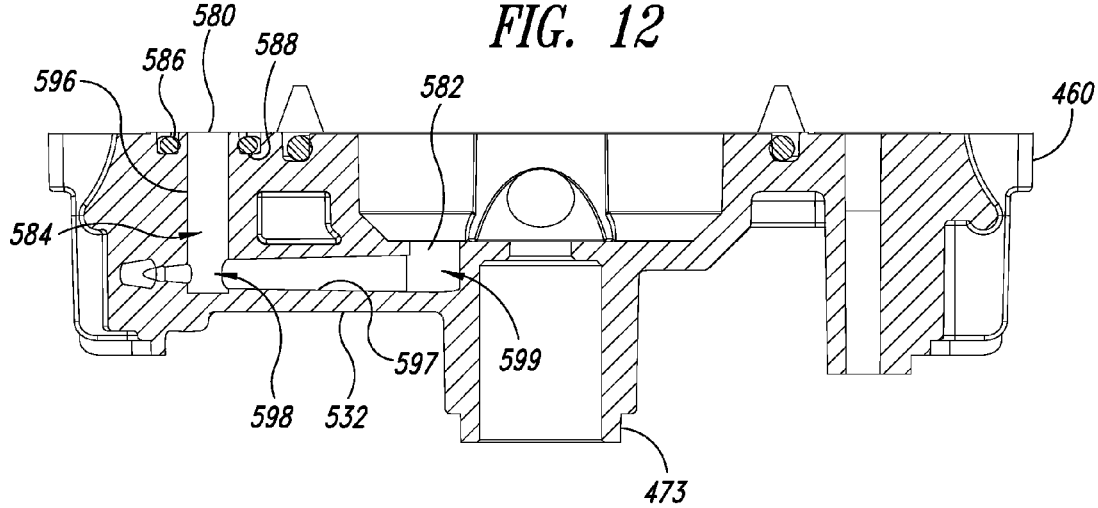
FIG. 13 is a cross-sectional view of the manifold of FIG. 9 taken along a line 13-13.
Figure 14:
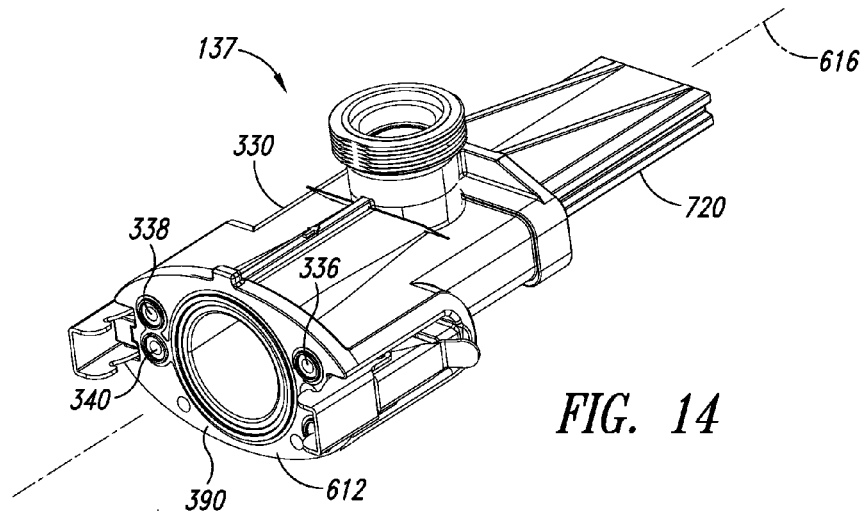
FIG. 14 is an isometric view of a mixing chamber assembly, in accordance with one embodiment.
Figures 15, 16, 17:
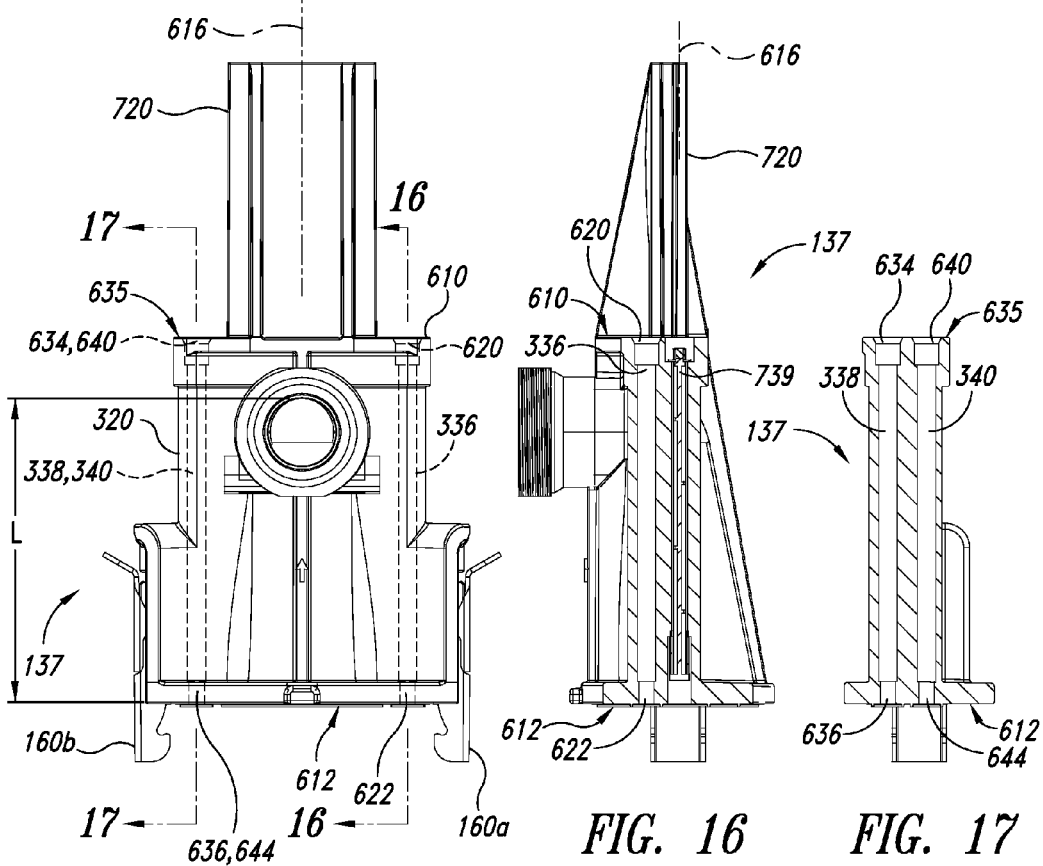
FIG. 15 is a plan view of the mixing chamber assembly of FIG. 14.
FIG. 16 is a cross-sectional view of the mixing chamber assembly of FIG. 15 taken along a line 16-16.
FIG. 17 is a cross-sectional view of the mixing chamber assembly of FIG. 15 taken along a line 17-17.

Referring to FIG. 6, a capillary tube 452 is positioned in a lumen 455 of an intermediate housing 456. A tip 457 of the capillary tube 452 is positioned adjacent to a throat 414. The sample can flow through the capillary tube 452 and into the throat 414. Pressurized fluid delivered through the port 420 proceeds along the outside of the intermediate housing 456 towards the throat 414. The flow of pressurized fluid is accelerated to form a high-pressure jet. The high-pressure jet draws the sample through the capillary tube 452 and, in some embodiments, helps to break up the sample into small droplets to produce a spray. The spray can be an aerosol, a fine spray, a mist, or the like and can flow out of an outlet 464. In some embodiments, the spray is a fine spray of an atomized sample.

The instrument 100 can use other types of nebulizers. Nebulizers include, but are not limited to, concentric tube nebulizers, fritted disc nebulizers, cross flow nebulizers, ultrasonic nebulizers, or other spray generating devices. U.S. Pat. No. 4,125,225 discloses nebulizers and components that can be modified or incorporated into the instrument 100. U.S. Pat. No. 4,125,225 is incorporated herein by reference in its entirety.

FIGS. 7 and 8 show the end cap assembly 170 with a multi-piece body 449 that can be held together by a plurality of fasteners 462*a*, 462*b*, 462*c* (collectively "462"). The body 449 includes a cover 450 and a manifold 454. The cover 450 can surround and protect internal components of the manifold 454.

The cover 450 includes a front plate 474 defining an aperture 476. An upper wall 480 and a lower wall 482 are spaced apart from one another to surround opposing sides of the manifold 454. Windows 490, 492 receive retention features 496, 498 of the manifold 454. When the cover 450 is coupled to the manifold 454, the upper and lower walls 480, 482 bear against a back plate 460, and a nozzle 510 is received by a cutout 500.

In other embodiments, the end cap assembly 170 can have a unitary construction. For example, the body of the end cap assembly can be monolithically formed via a molding process (e.g., an injection molding process, a compression molding process, etc.), machining process, or the like.

The manifold 454 of FIGS. 9 and 10 includes a tubular member 472, a pressurized fluid conduit 520, a fuel conduit 530, and an oxidant conduit 532. The tubular member 472 has a stepped end 473 receivable in the aperture 476 (FIG. 7). The conduits 520, 530, 532 can be generally similar to each other and the description of one conduit applies equally to the others, unless indicated otherwise.

Referring to FIG. 11, the pressurized fluid conduit 520 extends from a feed inlet 531 to a feed outlet 537 and can be formed, at least in part, of a rigid or flexible tube, pipe, or other type of single or multi-lumen conduit. A sealing member 536 is positioned in a recess 541 and surrounds the inlet 531. A feed passageway 534 extends between the feed inlet 531 and the feed outlet 537.

In some embodiments, including the illustrated embodiment of FIG. 11, the passageway 534 includes a first channel 535, a second channel 543, and a nonlinear section 538 therebetween. The first channel 535 extends from a back face 539 to the nonlinear section 538. The second channel 537 extends from the nonlinear section 538 to the feed outlet 537. The nonlinear section 538 is configured to receive a fluid flowing through the first channel 535 and redirects the fluid flow towards the feed outlet 537. The nonlinear section 538 can define an angle α in a range of about 90 degrees to about 130 degrees. Other configurations (e.g., angled configurations, curved configurations, or the like) are also possible.

FIG. 12 shows the fuel conduit 530 generally including a feed inlet 550, a feed outlet 552, and a feed passageway 554. The feed outlet 552 is downstream of outlet 537 (FIG. 11) and is positioned to deliver fuel directly into the mixing chamber 220. A sealing member 556 is positioned within a recess 558 and surrounds the feed inlet 550. The feed passageway 554 is generally U-shaped (as viewed from above in FIG. 12) and generally includes a first channel 566, a second channel 567, and nonlinear sections 568, 569.

FIG. 13 shows the oxidant conduit 532. The oxidant conduit 532 generally includes a feed inlet 580, a feed outlet 582, and a feed passageway 584. The outlet 582 is downstream of the outlet 537 (FIG. 11) and is positioned to deliver oxidant directly into the mixing chamber 220. A sealing member 586 is positioned within a recess 588 and surrounds the feed inlet 580. The passageway 584 includes a first channel 596, a second channel 597, and nonlinear sections 598, 599.

Referring again to FIG. 2, a nebulizer receiving channel 601 of the tubular member 472 receives a section of the nebulizer 210 carrying the sealing members 444. An output end of the nebulizer 210 is positioned to deliver the spray 218 directly into the mixing chamber 220. In the illustrated embodiment, the nebulizer 210 can bear against an inwardly extending flange 603 to limit axial movement of the nebulizer 210. The manifold 454 includes a recessed region 467. The recessed region 467 and the lumen 360 define the mixing chamber 220. The mixing chamber 220 narrows towards the burner 140 to accelerate the flow.

Referring to FIG. 14, the internal delivery passageways 336, 338, 340 extend generally parallel to a longitudinal axis 616 of the mixing chamber assembly 137. The passageway 336 can deliver a high-pressure fluid to the feed inlet 531 (FIG. 11). The passageway 338 can deliver fuel to the feed inlet 550. The passageway 340 delivers oxidant to the feed inlet 580. The sealing members 536, 556, 586 can seal the end cap assembly 170 with the end 390.

Referring to FIGS. 15 and 16, the passageway 336 includes a delivery inlet 620 and a delivery outlet 622 and extends past the entire longitudinal length of the mixing chamber 220. The passageway 336 is a generally straight through-hole.

FIG. 17 shows the passageways 338, 340. The passageway 338 includes a delivery inlet 634 positioned along a rear face 635 and a delivery outlet 636 positioned along the front face 612. The passageway 340 includes a delivery inlet 640 positioned along the rear face 635 and a delivery outlet 644 positioned along the front face 612. The passageways 338, 340 have longitudinal lengths that are longer than an axial length L (FIG. 15) of the lumen 360 (FIG. 3).

Referring to FIGS. 19-22, the latch mechanism 160a includes a base 650a, a lever arm 670a rotatable about an axis of rotation 671a, and a pulling member in the form of a hook member 674a. The hook member 674a is rotatable about an axis of rotation 672a. A pin 673 defines the axis of rotation 672a about which the hook member 674a. A pin 675 defines the axis of rotation 671a. The base 650a is coupled to the main body 330 by fasteners 652a, 653a, illustrated as bolts. A positioning element 660 (FIG. 20) can move the base 650a forwardly or rearwardly to adjust the compression the sealing members 536, 556, 586 (FIGS. 11-13). For example, to increase the pulling force applied to the end cap assembly 170, the positioning element 660 can be rotated to move the latch mechanism 160a rearwardly, as indicated by an arrow 664. To decrease the applied force, the positioning element 660 can be rotated in the opposite direction to move the latch mechanism 160a forwardly, as indicated by an arrow 662. The illustrated positioning element 660 is a set screw in a hole 663a. The end 661 of the set screw 660 engages threads of an internally threaded hole 665 in the base 650a. Other types of positioning elements can also be used, if needed or desired.

Figure 20:
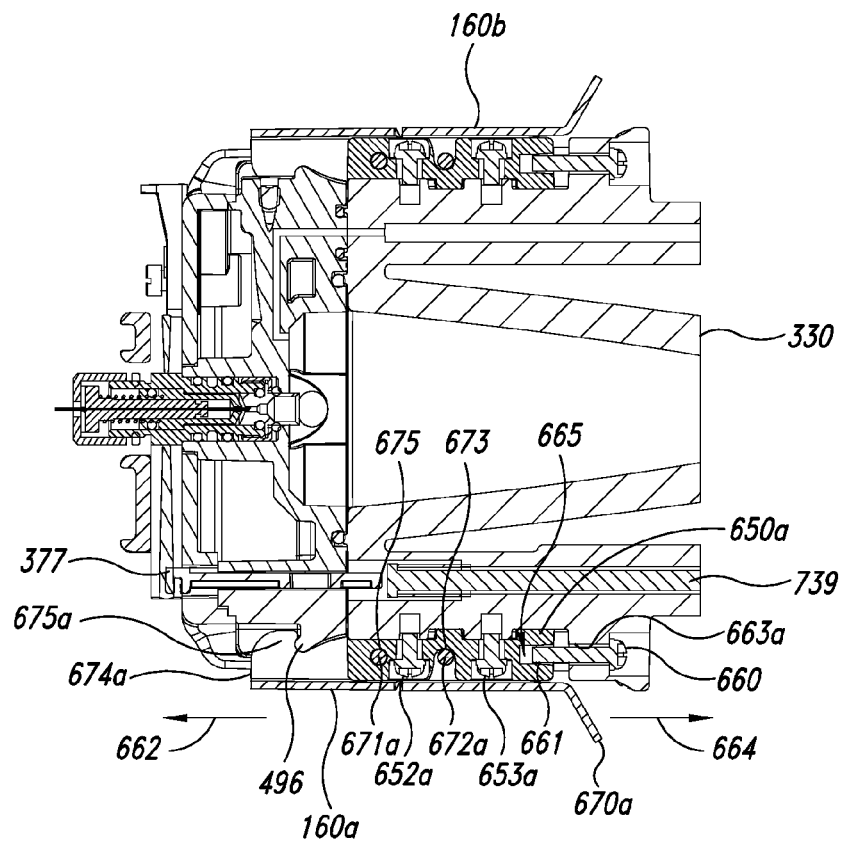
FIG. 20 is a cross-sectional view of a portion of the burner system of FIG. 19 taken along a line 20-20.
Figure 21:
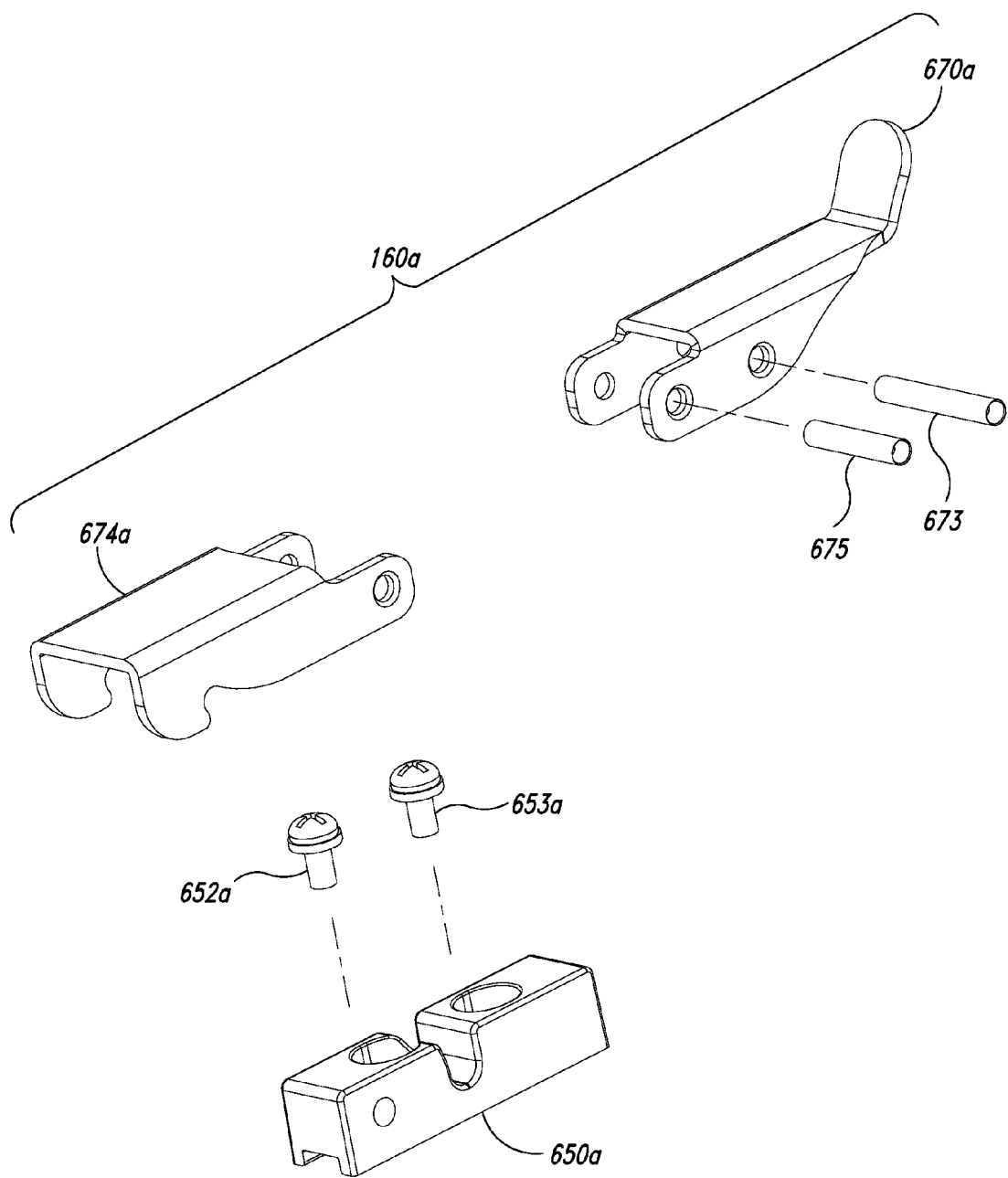
FIG. 21 is an exploded isometric view of a latch mechanism, in accordance with one embodiment.
Figure 22:
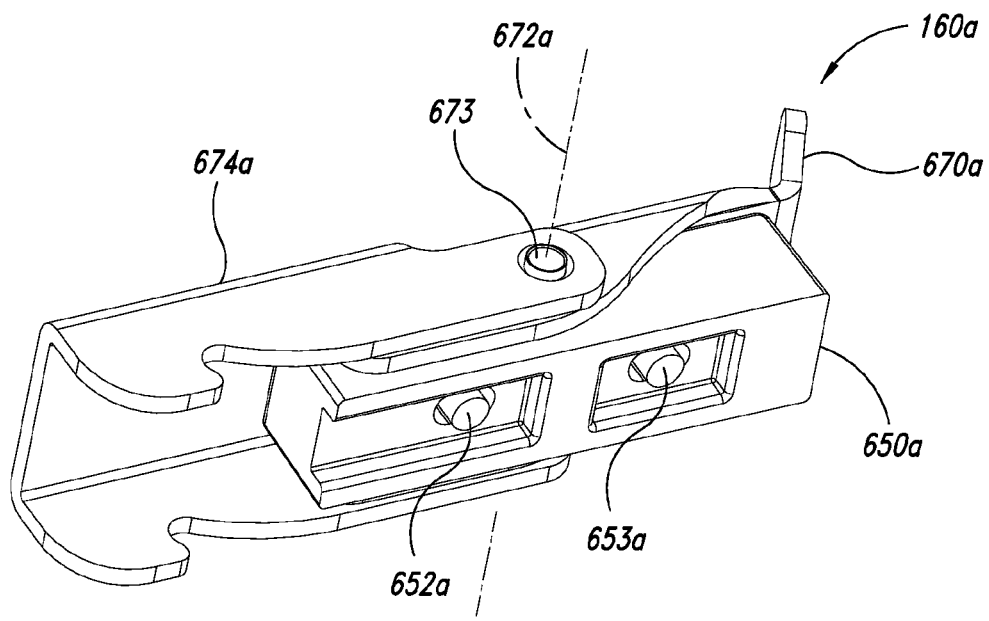
FIG. 22 is a front, bottom, and left side isometric view of the latch mechanism of FIG. 21.
Figure 23A:
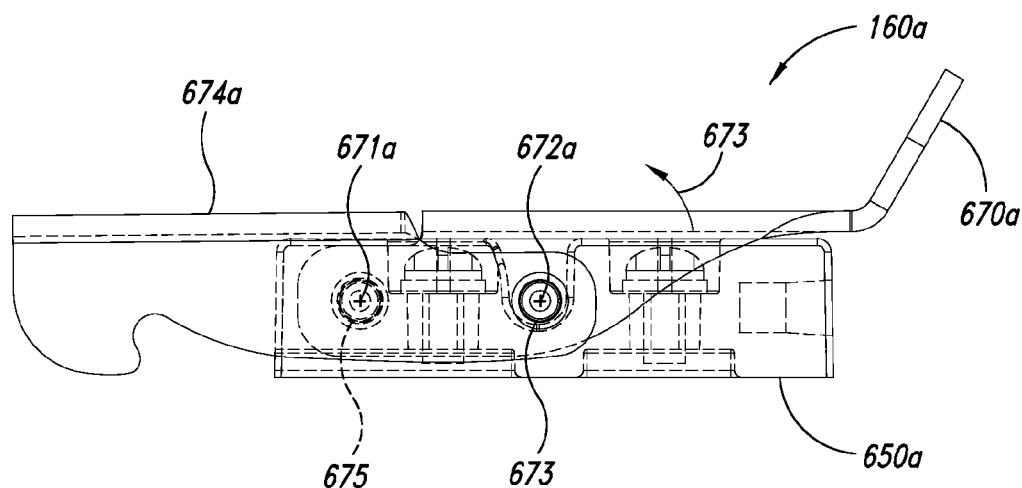
FIG. 23A is a side view of a latch mechanism in a latched configuration.
Figure 23B:
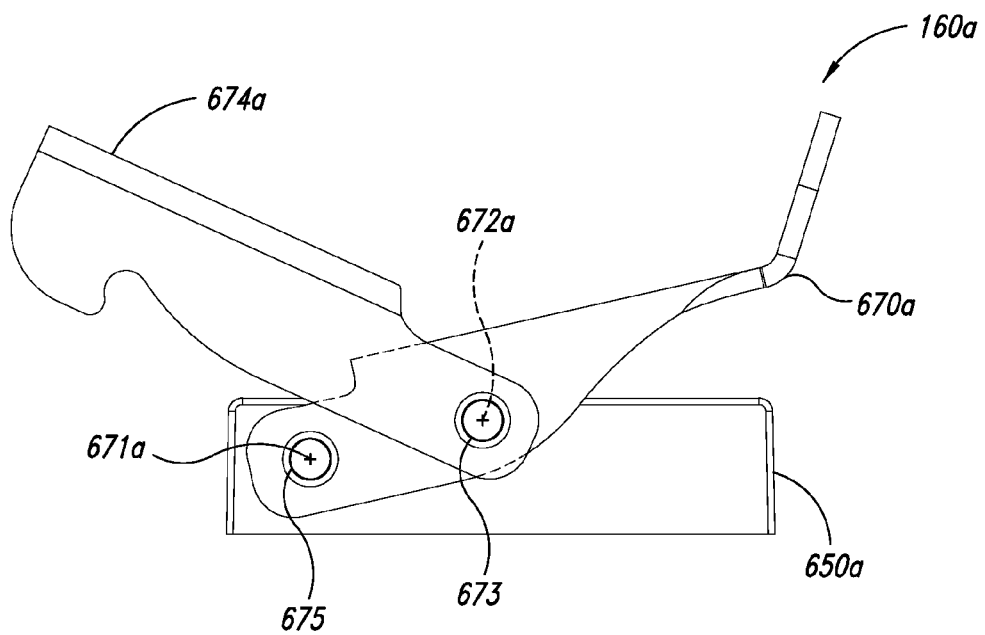
FIG. 23B is a side view of a latch mechanism in an unlatched configuration.
Figure 24:
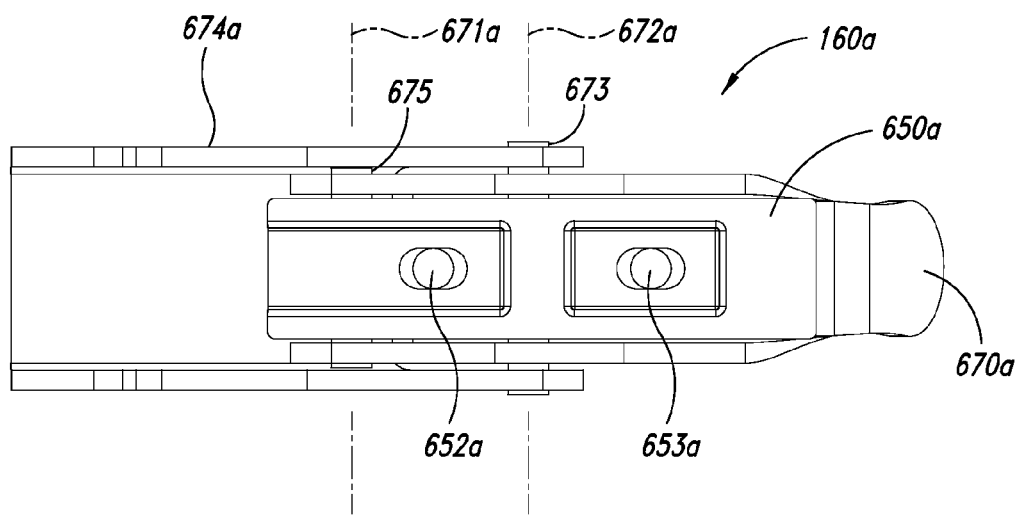
FIG. 24 is a bottom elevational view of the latch mechanism of FIG. 21.

FIG. 23A shows the latch mechanism 160a in a latched configuration. The lever arm 670a can be rotated (indicated by an arrow 673) to move the latch mechanism 160a towards an unlatched configuration of FIG. 23B. When unlatched, the hook member 674a can partially engage the retention feature 496, as shown in FIG. 20. As the latch mechanism 160a is moved to the latched configuration, it pulls the end cap assembly 170 to provide clamp-up forces sufficient to seal the mixing chamber 220. Other types of latch mechanisms can also be used. Latch mechanisms may include, without limitation, hooks, levers, handles, pins, or other components.

Figure 25:
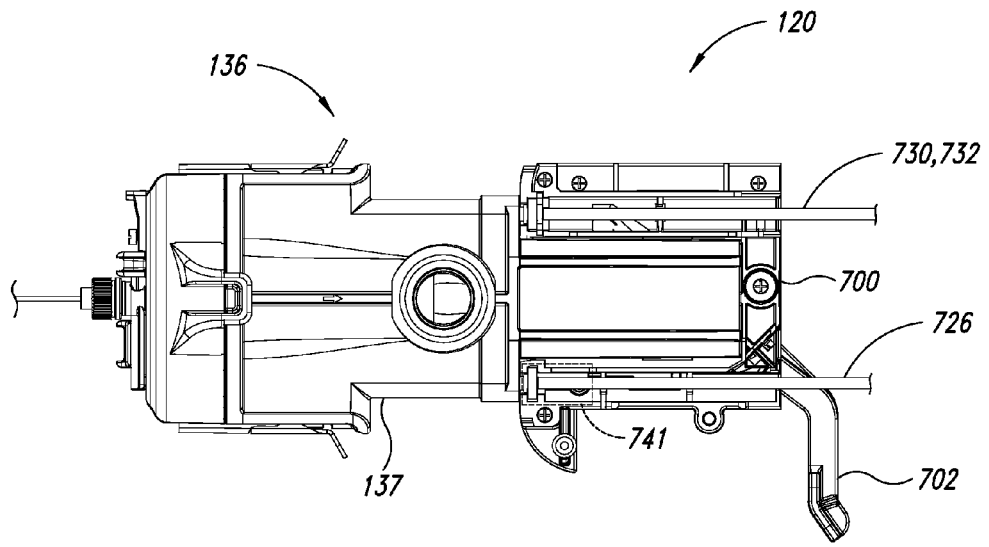
FIG. 25 is a plan view of a mixing apparatus docked in a docking station.
Figure 26A:
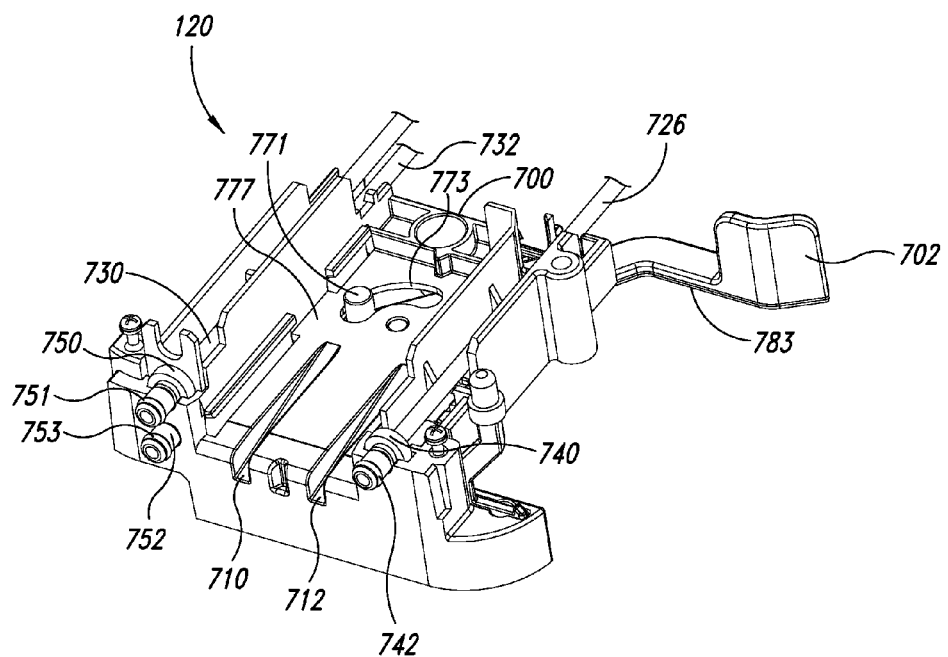
FIG. 26A is an isometric view of a docking station, in accordance with one embodiment.

FIGS. 25 and 26A show the docking station 120 including a tray 700 and a lever 702. The tray 700 includes contours 710, 712 configured to accommodate a projection 720 (FIG. 2) of the main body 330 positioned in a slot 731 (FIG. 2). Lines 726, 730, 732 can be fluidically coupled to the passageways 336, 338, 340 and can include, without limitation, conduits, hoses, pipes, or any other structures through which a substance can travel.

FIG. 25 shows a sensor 741 (e.g., a proximity sensor, a pressure sensor, a contact sensor, etc.) that can detect the nebulizer. A rod 739 (FIG. 20) can be moved when the sensor 377 (FIG. 3) is depressed by the nebulizer arm 376. Movement of the rod 739 can be detected by the sensor 741 (shown in phantom in FIG. 25). If the sensor 741 is a proximity sensor, the rod 739 can comprise a magnetic material.

The sensor 741 can send at least one signal to the controller 326. The controller 326 can notify a user if the nebulizer 210 is not properly installed. In some embodiments, the controller 326 can automatically prevent the flow of fluid (e.g., pressurized fluid, fuel, and oxidant) to the mixing apparatus 136 if the nebulizer 210 is not installed.

Referring to FIG. 26A, the line 726 has a fitting 740 that can be inserted into the delivery inlet 620. The fitting 740 includes a sealing member 742. The fluid line 730 includes a fitting 750 with a sealing member 751 that can be inserted into the delivery inlet 634. The fluid line 732 includes a fitting 752 with a sealing member 753 that can be inserted into the delivery inlet 640.

To assemble the instrument 100, the latch mechanisms 160a, 160b can sealingly couple the end cap assembly 170 to the mixing chamber assembly 137. The applied forces can be increased or decreased to achieve a desired fit. To install the mixing apparatus 136, the projection 720 can be inserted into the slot 731 (FIG. 2) between the tray 700 and the ignition system 146. As the projection 720 slides towards the rear of the tray 700, the inlets 620, 634, 640 can receive the fittings 740, 750, 752, respectively.

Figure 18:
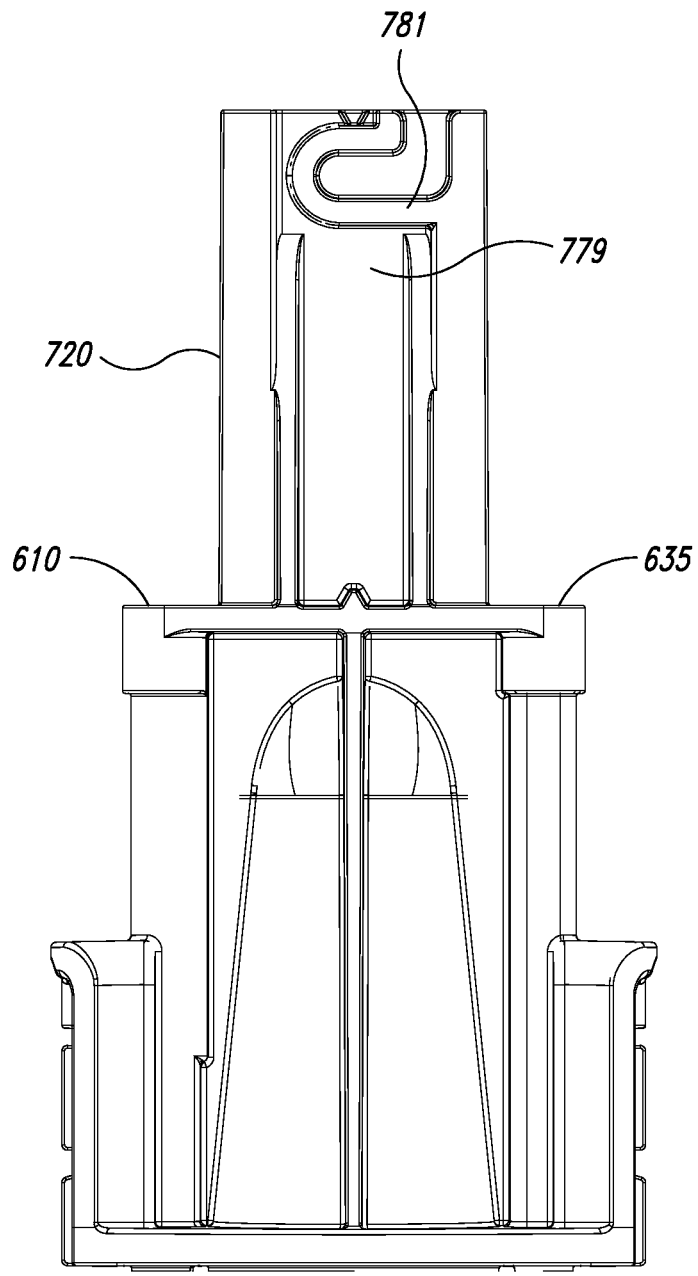
FIG. 18 is a bottom view of a main body of a mixing chamber assembly.
Figure 19:
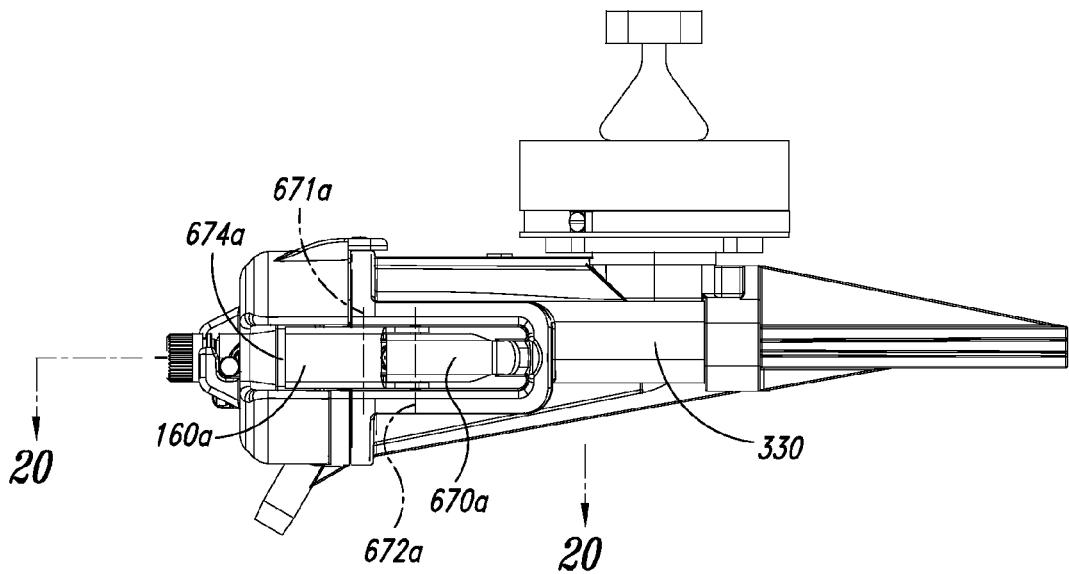
FIG. 19 is a side elevational view of a burner system.
Figure 26B:
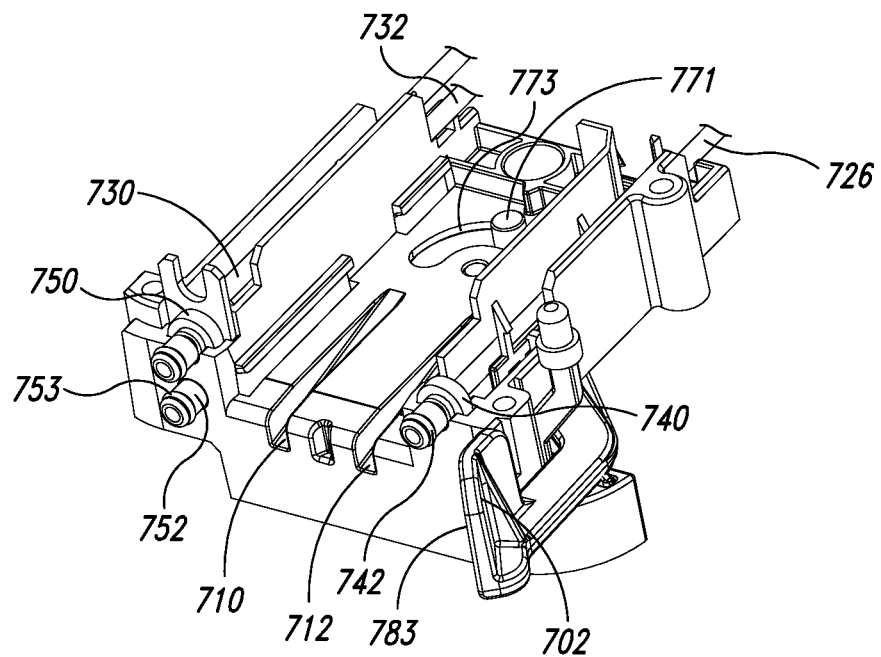
FIG. 26B is an isometric view of the docking station of FIG. 26A with a lever in an open configuration.

A protrusion 771 (FIG. 26A) can be received in a recessed region 779 (FIG. 18). As the lever 702 is rotated from an open position (FIG. 26A) to a closed position (FIG. 26B), the protrusion 771 moves along a slot 773 and slides along a wall 781 (FIG. 18) to push the mixing chamber assembly 137 rearwardly. To remove the mixing apparatus 136, a user can move the lever 702 to the open position. The mixing apparatus 136 can be pulled from the docking station 120 and can be replaced or disassembled, if needed or desired.

The components and features disclosed herein can be used with a wide range of different types of spectroscopy instruments or other types of instruments that analyze substances. For example, the mixing apparatus 136 can be modified and used with different types of instruments that analyze flames based on absorption, emission, or fluorescence by atoms or elementary ions. The embodiments, features, systems, devices, materials, methods and techniques described herein may, in some embodiments, be similar to any one or more of the embodiments, features (e.g., pressurization sources, nebulizers, burners, etc.), systems, devices, materials, methods and techniques described in U.S. Pat. Nos. 4,125,225; 4,606,718; 4,776,694; 4,886,359; and 6,222,626. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. Pat. Nos. 4,125,225; 4,606,718; 4,776,694; 4,886,359; and 6,222,626. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An atomic absorption instrument, comprising:
   a burner; and
   a mixing apparatus for delivering a combustible mixture to the burner, the mixing apparatus including
   a mixing chamber assembly including a main body and a plurality of internal delivery passageways extending through the main body towards an end of the mixing chamber assembly, the internal delivery passageways being located between an exterior surface of the main body and an interior surface of the main body, the interior surface defining at least a portion of a mixing chamber through which the combustible mixture flows towards the burner, and
   an end cap assembly configured to hold a nebulizer, the end cap assembly including a plurality of internal feed passageways through which fluid from the internal delivery passageways flows into the mixing chamber when the end cap assembly is coupled to the end of the mixing chamber assembly, wherein
   at least one of the internal feed passageways has at least one angled section configured to receive a fluid flow and to redirect the fluid flow towards the mixing chamber.

2. The atomic absorption instrument of claim 1, wherein the at least one internal feed passageway includes a first channel extending from the angled section towards one of the internal delivery passageways and a second channel extending from the angled section towards the mixing chamber when the end cap assembly is coupled to the mixing chamber assembly.

3. The atomic absorption instrument of claim 1, further comprising:
at least one sealing member surrounding one of the internal feed passageways, the sealing member compressed between the end cap assembly and the mixing chamber assembly to form a seal when the end cap assembly is coupled to the main body.

4. The atomic absorption instrument of claim 1, further comprising:
a docking station configured to receive the mixing chamber assembly and to deliver fluids to the internal delivery passageways.

5. The atomic absorption instrument of claim 4, wherein the docking station comprises a plurality of fittings that sealingly couple fluid lines to respective internal delivery passageways.

6. The atomic absorption instrument of claim 4, further comprising:
a source of pressurized fluid;
an oxidant source; and
a fuel source;
wherein the docking station delivers pressurized fluid from the source of pressurized fluid, oxidant from the oxidant source, and fuel from the fuel source to a portion of the mixing chamber assembly positioned under the burner.

7. The atomic absorption instrument of claim 1, further comprising:
at least one latch mechanism movable between an unlatched configuration and a latched configuration, the at least one latch mechanism is configured to pull the end cap assembly towards the end of the mixing chamber assembly.

8. The atomic absorption instrument of claim 7, wherein the at least one latch mechanism includes a lever arm that rotates to move the latch mechanism from the unlatched configuration to the latched configuration.

9. The atomic absorption instrument of claim 7, wherein the at least one latch mechanism includes a first latch mechanism and a second latch mechanism, the first latch mechanism and the second latch mechanism are positioned at opposing sides of the mixing chamber assembly and are positioned to engage retention features of the end cap assembly.

10. The atomic absorption instrument of claim 1, further comprising:
a controller; and
a sensor configured to detect the nebulizer and communicatively coupled to the controller, wherein the controller commands the atomic absorption instrument based on at least one signal from the sensor.

11. The atomic absorption instrument of claim 1, wherein at least one of the internal delivery passageways extends past at least most of a longitudinal length of the mixing chamber.

12. The atomic absorption instrument of claim 1, wherein at least one of the internal delivery passageways has a longitudinal length that is longer than a length of a portion of the mixing chamber extending along a longitudinal axis of the mixing chamber assembly.

13. An atomic absorption instrument, comprising:
a burner; and
a mixing apparatus for delivering a combustible mixture to the burner, the mixing apparatus including:
a mixing chamber assembly including a main body and a plurality of internal delivery passageways extending through the main body towards an end of the mixing chamber assembly, the internal delivery passageways being located between an exterior surface of the main body and an interior surface of the main body, the interior surface defining at least a portion of a mixing chamber through which the combustible mixture flows towards the burner, and
an end cap assembly configured to hold a nebulizer, the end cap assembly including a plurality of internal feed passageways through which fluid from the internal delivery passageways flows into the mixing chamber when the end cap assembly is coupled to the end of the mixing chamber assembly, wherein
the main body includes a plurality of delivery inlets and a plurality of delivery outlets, each internal delivery passageway extends between one of the delivery inlets and a respective one of the delivery outlets, the end cap assembly comprises a plurality of feed inlets and a plurality of feed outlets, each internal feed passageway extends between one of the feed inlets and a respective one of the feed outlets, the feed inlets configured to receive at least one fluid from respective delivery outlets of the main body such that the at least one fluid can flow through the internal feed passageways and the feed outlets, and into the mixing chamber when the end cap assembly is coupled to the main body.

14. An atomic absorption instrument, comprising:
a burner; and
a mixing apparatus for delivering a combustible mixture to the burner, the mixing apparatus including
a mixing chamber assembly including a main body and a plurality of internal delivery passageways extending through the main body towards an end of the mixing chamber assembly, the internal delivery passageways being located between an exterior surface of the main body and an interior surface of the main body, the interior surface defining at least a portion of a mixing chamber through which the combustible mixture flows towards the burner, and
an end cap assembly configured to hold a nebulizer, the end cap assembly including a plurality of internal feed passageways through which fluid from the internal delivery passageways flows into the mixing chamber when the end cap assembly is coupled to the end of the mixing chamber assembly, wherein
the plurality of internal delivery passageways includes a pressurized fluid delivery passageway, a fuel delivery passageway, and an oxidant delivery passageway, wherein the plurality of internal feed passageways includes a pressurized fluid feed passageway through which pressurized fluid from the pressurized fluid delivery passageway flows to the nebulizer, a fuel feed passageway through which fuel from the fuel delivery passageway flows into the mixing chamber, and an oxidant feed passageway through which oxidant from the oxidant delivery passageway flows into the mixing chamber.

15. An end cap assembly for a mixing apparatus of an atomic absorption instrument, the end cap assembly comprising:
a first face for mating with a mixing chamber assembly;
a second face opposing the first face;

a nebulizer receiving channel extending through a main body, the nebulizer receiving channel is dimensioned such that a port of a nebulizer is positioned within the nebulizer receiving channel and an outlet of the nebulizer is positioned to deliver a spray in a mixing chamber when the end cap assembly carries the nebulizer and is coupled to the mixing chamber assembly; and a manifold including a plurality of fluid passageways extending from the first face, one of the fluid passageways delivers a first fluid from the mixing chamber assembly to the nebulizer and another one of the passageways delivers a second fluid from the mixing chamber assembly to the mixing chamber.

16. The end cap assembly of claim 15, wherein at least one of the fluid passageways includes an angled section that receives fluid flowing towards the second face and directs the fluid inwardly towards an inlet port positioned along the nebulizer receiving channel.

17. The end cap assembly of claim 15, further comprising:

a plurality of sealing members surrounding respective fluid passageways and forming seals between the end cap assembly and the mixing chamber assembly when the end cap assembly is coupled to the mixing chamber assembly.

18. The end cap assembly of claim 15, further comprising:

a cover that couples to a back plate of the manifold to cover conduits of the manifold, the conduits defines fluid passageways.

19. The end cap assembly of claim 15, wherein the manifold includes a tubular member defining the nebulizer receiving channel and extending through an opening in the cover.

* * * * *